(12) United States Patent
Brustad

(10) Patent No.: US 7,235,062 B2
(45) Date of Patent: Jun. 26, 2007

(54) SURGICAL ACCESS DEVICE WITH FLOATING GEL SEAL

(75) Inventor: John R. Brustad, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 941 days.

(21) Appl. No.: 10/056,831

(22) Filed: Jan. 24, 2002

(65) Prior Publication Data

US 2003/0139756 A1 Jul. 24, 2003

(51) Int. Cl.
*A61M 5/178* (2006.01)

(52) U.S. Cl. .................................. 604/167.02

(58) Field of Classification Search ................. 604/167, 604/280, 256, 249, 264, 160, 161
See application file for complete search history.

(56) References Cited

U.S. PATENT DOCUMENTS

| | | | |
|---|---|---|---|
| 4,475,548 A * | 10/1984 | Muto ..................... | 128/207.14 |
| 4,895,565 A | 1/1990 | Hillstead | |
| 5,209,737 A | 5/1993 | Ritchart | |
| 5,360,417 A * | 11/1994 | Gravener et al. ........... | 604/278 |
| 5,385,553 A | 1/1995 | Hart | |
| 5,389,080 A * | 2/1995 | Yoon ..................... | 604/167.03 |
| 5,407,433 A | 4/1995 | Loomas ................... | 604/167 |
| 5,411,483 A | 5/1995 | Loomas et al. ............ | 604/167 |
| 5,429,609 A * | 7/1995 | Yoon ..................... | 604/167.03 |
| 5,441,486 A * | 8/1995 | Yoon ..................... | 604/167.03 |
| 5,634,908 A | 6/1997 | Loomas ................... | 604/167 |
| 5,634,911 A * | 6/1997 | Hermann et al. ........... | 604/256 |
| 5,788,676 A * | 8/1998 | Yoon ..................... | 604/167.03 |
| 5,814,026 A * | 9/1998 | Yoon ..................... | 604/539 |
| 5,820,606 A | 10/1998 | Davis et al. .............. | 604/256 |
| 5,865,807 A | 2/1999 | Blake, III | |
| 5,913,847 A * | 6/1999 | Yoon ..................... | 604/523 |

FOREIGN PATENT DOCUMENTS

WO       WO 02/34108 A2    5/2002

* cited by examiner

*Primary Examiner*—Manuel Mendez
(74) *Attorney, Agent, or Firm*—David G. Majdali; Kenneth K. Vu; Richard L. Myers

(57) ABSTRACT

A trocar is provided with a cannula and a housing and valve assembly disposed in the housing which forms a housing seal, and instrument seal, and in some cases a zero seal. A gel material is included in the valve and provides the valve with superior flotation properties for maintaining the instrument seal even when the instrument is moved off-axis. In order to accommodate movement of the gel material, voids can be formed within the valve housing and even within the gel material.

17 Claims, 4 Drawing Sheets

SURGICAL ACCESS DEVICE WITH FLOATING GEL SEAL

BACKGROUND OF THE INVENTION

1. Field of the Invention

This invention relates generally to surgical access devices and more specifically to valves and seals associated with such devices.

2. Discussion of the Related Art

Access devices are commonly used to facilitate the introduction of surgical instruments into body conduits and body cavities. One such device, which is typically referred to as a trocar, is used in laparoscopic procedures to provide access through the abdominal wall and into the abdominal cavity. In laparoscopic surgeries, the abdominal cavity is commonly inflated or insufflated in order to increase the volume of the working environment. Under these circumstances, valves are provided in a valve housing of the trocar to inhibit the escape of the insufflation gas. The valves form an instrument seal in the presence of an instrument, and a zero seal in the absence of an instrument.

Trocar seals are disclosed and claimed in applicant's U.S. Pat. No. 5,385,553, which is incorporated herein by reference. This patent discusses the problems which can be encountered when the instrument is inserted off-axis. The solution of floating the valve is discussed in detail.

In this patent it is contemplated that the valve would comprise first portions which define an orifice through the valve and second portions disposed outwardly of the first portions. These second portions are intended to provide a greater flexibility than the first portions. As a consequence, when an instrument is inserted off-axis, the second portions will deform while the first portions, which form the instrument seal, will remain undeformed. One of the embodiments contemplates provision of an excess of material disposed outwardly of the valve orifice which functions generally as a bellows. In this case the first portions of the valve have a first radial length to radial distance ratio while the second portions of the valve have a second radial length to radial distance ratio. The valving mechanism is formed generally of a solid but elastomeric material.

SUMMARY OF THE INVENTION

In accordance with the present invention, an access device is provided, for example, in the form of a trocar having a valve housing. In this case, a valve assembly is disposed in the housing and includes a gel material which has superior sealing characteristics and flotation properties. In some respects, the gel is a solid in that it has a generally fixed volume. On the other hand, the gel functions somewhat like a liquid in that it tends to "flow." Other characteristics of the gel material, such as an elongation greater than 1000 percent, a low durometer and an excellent tear strength are disclosed and claimed in applicant's International Application No. PCT/US01/29682. This application, which was filed on Sep. 21, 2001 and entitled "Surgical Access Apparatus and Method", is incorporated herein by reference.

The gel material will typically form a seal with the valve housing and may also be used to form the instrument seal as well as the zero seal. Alternatively, the valve assembly can be formed with a typical septum valve supported by the gel material to provide the septum valve with the superior flotation properties.

In order to facilitate compression of the gel material, voids can be created in the housing or even within the gel material to accommodate compression of the material during insertion of an instrument.

ASPECTS OF THE INVENTION

In one aspect of the invention, a trocar has an axis and is adapted to provide access for a surgical instrument across a body wall and into a body cavity. A cannula, disposed along the axis, has a proximal end and a distal end, and is adapted for disposition across the body wall. A housing disposed along the access at the proximal end of the cannula is adapted to receive the surgical instrument and to introduce the instrument into the cannula. A valve is disposed in the housing and provided with properties for forming a first seal with the housing wall, a second seal with the instrument when it is present in the trocar and a third seal with itself when the instrument is absent from the trocar. A gel material included in the valve has flotation properties for maintaining the second seal even when the surgical instrument is moved laterally of the axis of the trocar.

In another aspect of the invention, a valve assembly includes a septum valve disposed in the valve housing and adapted to form a first seal with the instrument when it is received into the trocar. A valve support is disposed between the septum valve and the housing to float the septum valve relative to the housing. The valve support includes a gel having elongation greater than 1000 percent to facilitate maintenance of the first seal during off-axis movement of the instrument relative to the housing. The septum valve can be insert molded to the valve support. In another aspect of the invention, a valve is disposed in the valve housing and adapted to form a seal with the instrument when the instrument is inserted through the valve housing and into the cannula. Portions of the valve include a gel material having properties for moving relative to the axis to maintain the seal with the instrument when the instrument is moved off-axis.

Voids can be formed in proximity to the gel material to facilitate movement of the material relative to the axis. These voids can be formed primarily on the walls of the valve housing, between the walls and the gel material and even within the gel material.

These and other features and advantages of the invention will become more apparent with a description of preferred embodiments in reference to the associated drawings.

DESCRIPTION OF PREFERRED EMBODIMENTS AND BEST MODE OF THE INVENTION

Figure 1:
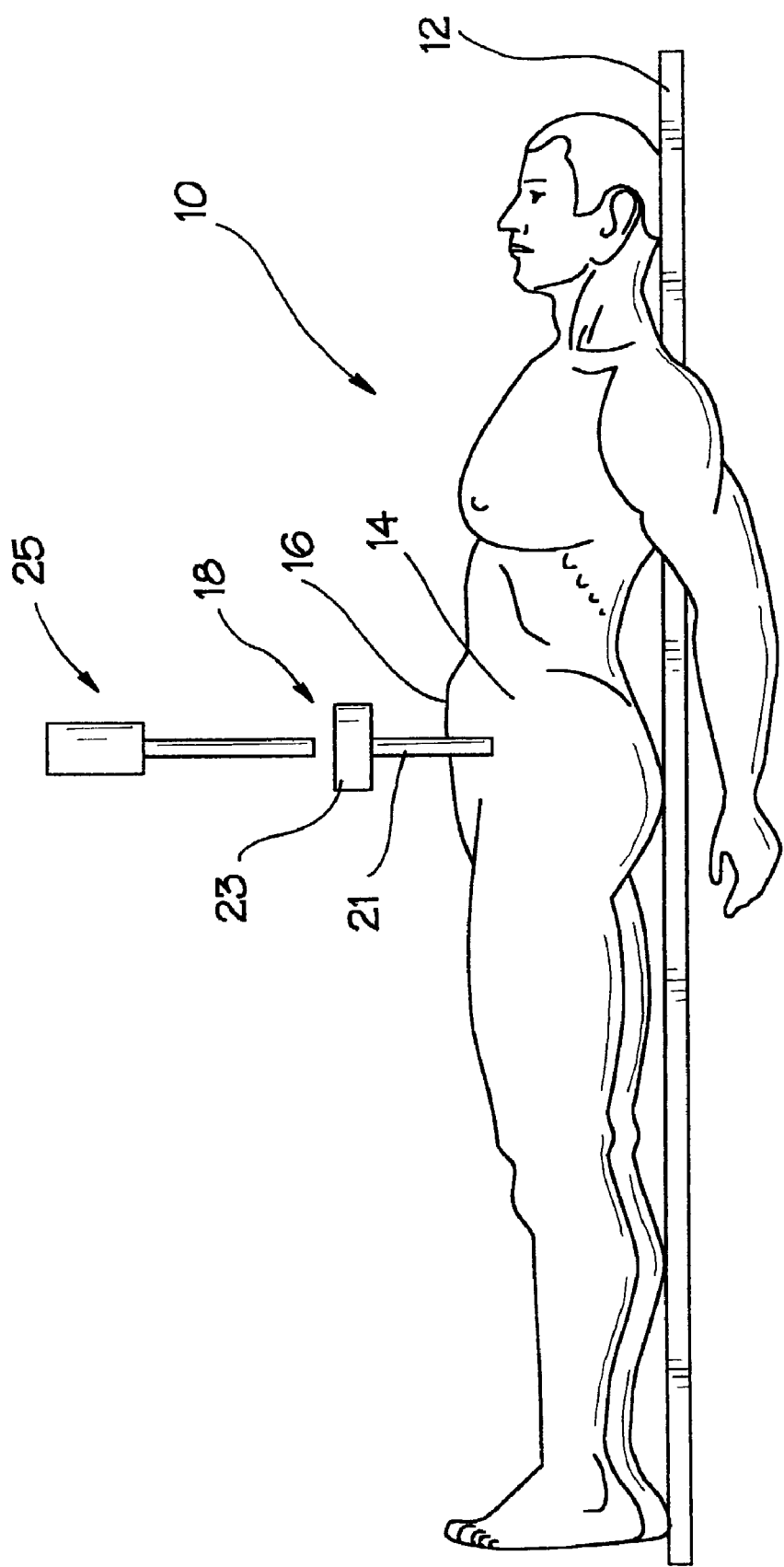
FIG. 1 is a side elevation view of a patent operatively position with a trocar extending into the abdominal cavity and providing access for a surgical instrument.

A patient is illustrated in FIG. 1 and designated generally by the reference numeral 10. The patient 10 is illustrated in a prone position on an operation table 12 where he is prepared for laparoscopic surgery. This type of surgery is performed within the patient's abdominal cavity 14 with minimal access through an abdominal wall 16. This access is typically provided by a trocar 18 having a cannula 21 and valve housing 23. The trocar 18 may be one of several trocars which are used simultaneously to provide access for surgical instruments such as the instrument 25 illustrates in the form of a laparoscope.

During a laparoscopic procedure the abdomen 14 is typically inflated with an insufflation gas, such as carbon dioxide, in order to distend the abdominal wall 16 and thereby increase the volume of the working environment. It is the purpose of the valve housing 23 and associated valves to maintain this insufflation gas within the abdominal cavity 14, both in the presence of the instrument 25 and in the absence of the instrument 25.

One embodiment of the trocar 18 of the present invention is illustrated in FIG. 2. In this detailed view, the trocar 18 is shown to include the cannula 21 with a working channel 26 (extending generally along an axis 27), a proximal end 30, and a distal end 32. The valve housing 23 is coupled to the distal end 32 in coaxial alignment with the cannula 21.

In this embodiment, the valve housing 23 is constructed with a cylindrical, vertical wall 34 and a pair of generally annular horizontal walls 36 and 38. The wall 36 can be disposed generally perpendicular to the axis 27 with portions defining an exterior opening 41 for instrument access.

In the illustrated embodiment, the wall 38 is generally parallel to the wall 36 and defines an interior opening 43 which communicates with the working channel (26) of the cannula 21.

A valve assembly 50 is illustrated within the valve housing 23 but could be disposed anywhere along the axis 27. The valve assembly 50 includes a block 52 of gel material 54. In this embodiment, the block 50 forms a housing seal 55 with the vertical wall 34 to prevent the leak of insufflation gases between the gel material 54 and the housing 23. The gel block 52 is further configured with a slit or opening 56 which in this embodiment extends along the axis 27. This opening 56 is perhaps best illustrated in the cross sectional views of FIGS. 2A and 2B.

Figure 2A:
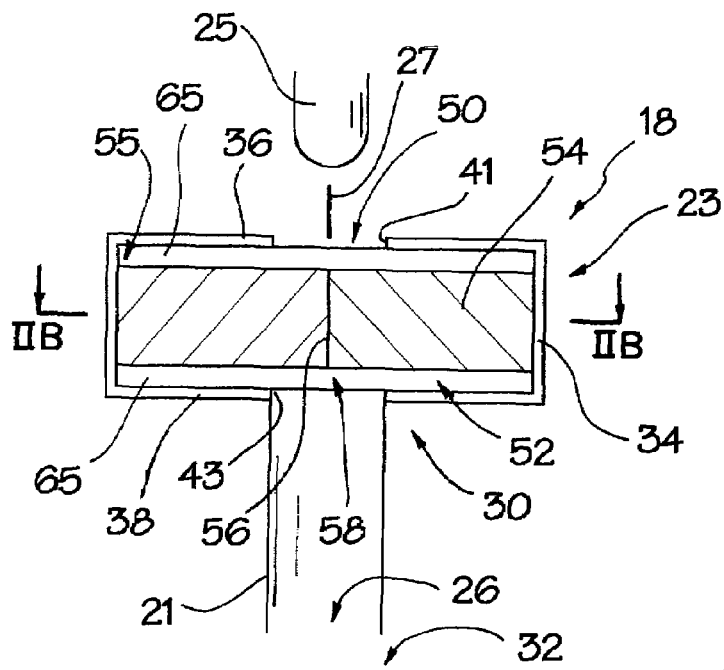
FIG. 2A is an axial cross section view of one embodiment of the trocar, and illustrates a zero seal configuration in the absence of the instrument.
Figure 2B:
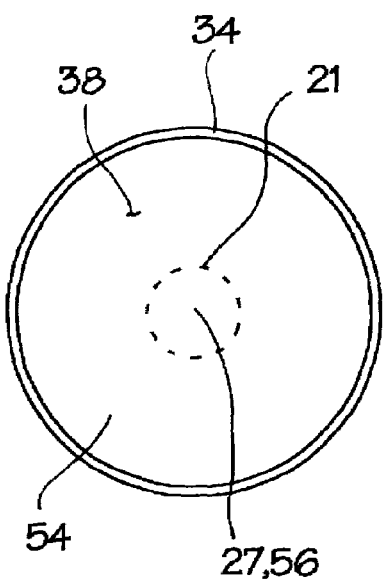
FIG. 2B is a cross section view taken along lines II B—II B of FIG. 2A.

In FIG. 2A, the valve assembly 50 is illustrated in the absence of the instrument 25 (FIG. 1). Under these circumstances, the gel material 54 closes the opening 56 to form a zero seal 58. The zero seal 58 in this embodiment is formed solely by the gel material 54, generally along the axis 27, and prevents the escape of insufflation gases through the gel block 52 in the absence of the instrument 25.

The gel block 52 is not merely a septum having only a thin dimension along the axis 27. Rather, the block 52 is preferably formed so that the ratio of its thickness to its outermost dimension, such as its radius, is in a range between one and five. The thickness of the block 52 is preferably in a range between five and ten millimeters. In a preferred embodiment, the gel block 52 in the relaxed state shown in FIG. 2A, has a thickness of about seven millimeters and an outermost dimension, such as its radius about 21 millimeters. (In this case the ratio is about three).

Figure 3:
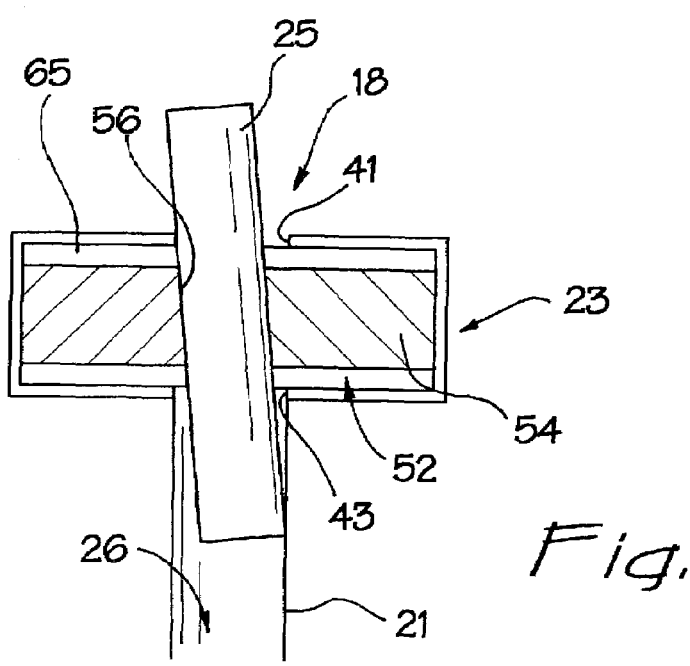
FIG. 3 is an axial cross section view of the trocar illustrating an instrument seal formed during off-axis insertion of the instrument.

Operation of the trocar 18 and associated valve assembly 50 is best illustrated in FIG. 3. In this case, the instrument 25 is illustrated to be inserted off-axis through the opening 56. In this view it can be seen that the portions of the gel material 54 which define the opening 56 of the block 52 also form an instrument seal 61 with the instrument 25. This instrument seal 61 prevents the escape of insufflation gases through the gel block 52 when the instrument 25 is present in the trocar 18.

FIG. 3 illustrates at least two aspects of the present invention, both of which relate to properties of the gel block 52 in the presence of the instrument 25. Initially, it will be noted that the instrument seal (61) will move with the instrument 25. Although the instrument 25 may be inserted along the axis 27, it may also be inserted off-axis or moved off-axis, as illustrated in FIG. 3, during the operation. Under these circumstances, it is important that the instrument seal 61 be maintained, or permitted to "float" with the off-axis movement of the instrument 25. The instrument seal 61 is formed by both the instrument 25 and the valve assembly 50; however, since the instrument 25 will typically be rigid, it is up to the valve assembly 50 to accommodate this flotation.

It is the properties of the gel material 54 which make it particularly desirable for flotation purposes. Properties of the gel material including elongation greater than 1,000 percent, low durometer, and high tear strength, are fully disclosed in the previously mentioned International Application Serial No. PCT/US01/29682.

Another aspect of the invention associated with insertion of the instrument 25 relates to movement of the gel material 54 as the opening 56 is spread by the instrument 25. As this opening 56 enlarges, the displaced gel material, which is generally non-compressible, will attempt to expand. In order to accommodate this expansion, it is desirable to provide air pockets or voids 65 into which the gel material 54 can move. These voids 65 are most prominently illustrated in FIG. 2A in the absence of the instrument 25.

Figure 4:
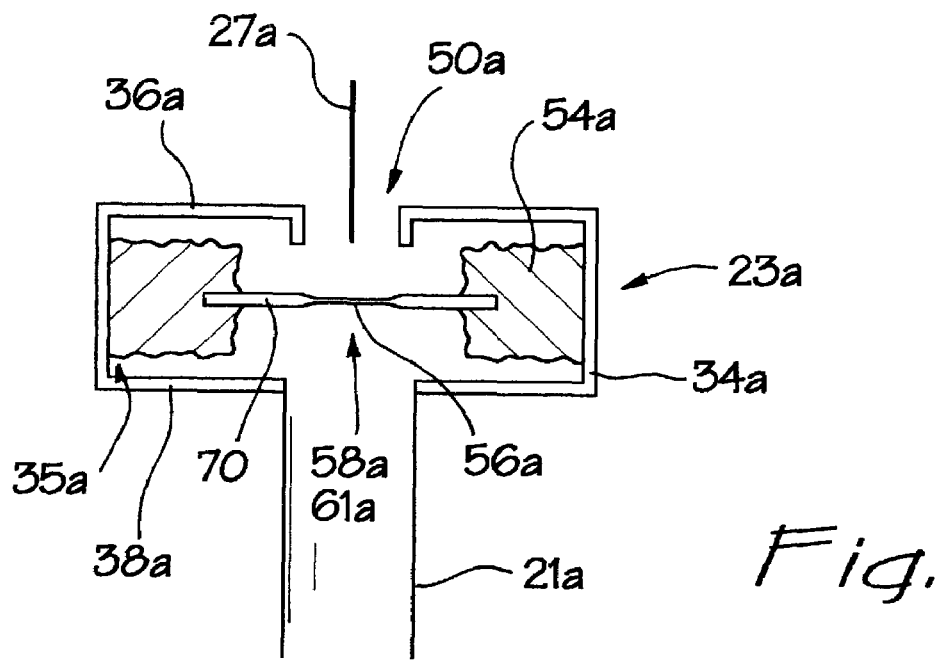
FIG. 4 is an axial cross section view of another embodiment of the invention including a septum seal and a floating gel support.

Another embodiment of the invention is illustrated in FIG. 4. In this embodiment, elements of structure similar to those previously discussed will be designated with the same reference numeral followed by the lower case letter "a." Thus the cannula is designated with the reference numeral 21a, the valve housing with the numeral 23a, and the valve assembly with the number 50a. In this embodiment, the valve assembly 50a includes a thin septum 70 with the opening 56a disposed generally along the axis 27a. The septum 70 will typically be formed of an elastomeric material and will be supported within the valve housing 23a by the gel material 54. In this case, the septum 70 is responsible for the zero seal 58a as well as the instrument seal 61a.

The gel material 54 forms a seal with the septum 70 as well as the housing seal 55a with the housing wall 34a. It will be noted that in this embodiment, the gel material 54 provides floating support for the septum 27. Any outward expansion required of the gel material can be accommodated by the voids 65a between the gel material 54 and the horizontal walls 36a and 38a.

Figure 5:
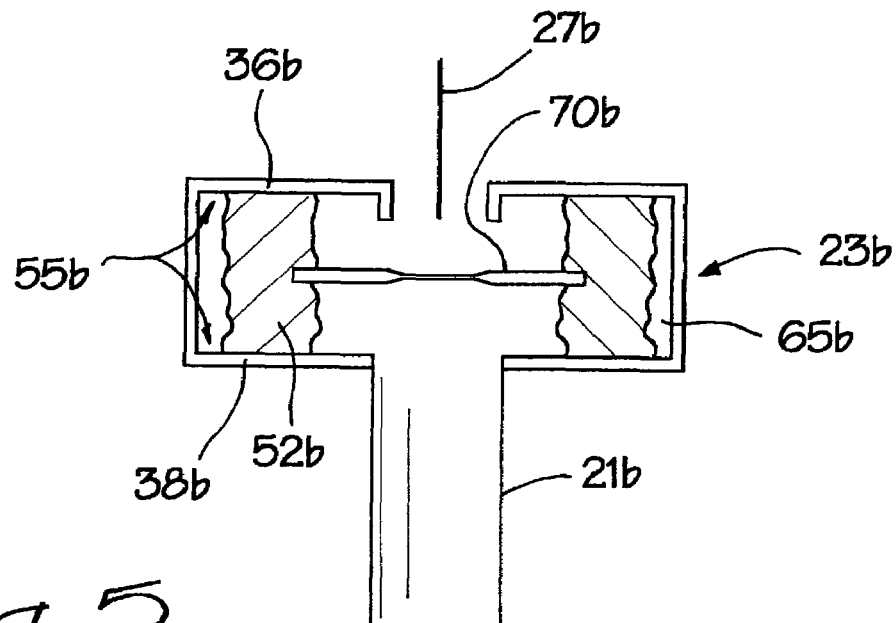
FIG. 5 is an axial cross section view of another embodiment of the valve apparatus.

A further embodiment of the invention is illustrated in FIG. 5, wherein elements of structure similar to those previously disclosed are designated with the same reference numeral followed by the lower case letter "b." The embodiment of FIG. 5 differs from that of FIG. 4 primarily in the location of the gel block 52b. In this case, the housing seal 55b is formed around the axis 27b between the gel block 52 and the horizontal walls 36b and 38b of the valve housing 23b. The voids 65b desired for expansion of the gel block 52b can be located between the vertical wall 34b and the gel block 52b. This embodiment could include the elastomeric septum 70b, or might comprise only the gel block 52b as illustrated in the embodiment of FIG. 2A.

Figure 6:
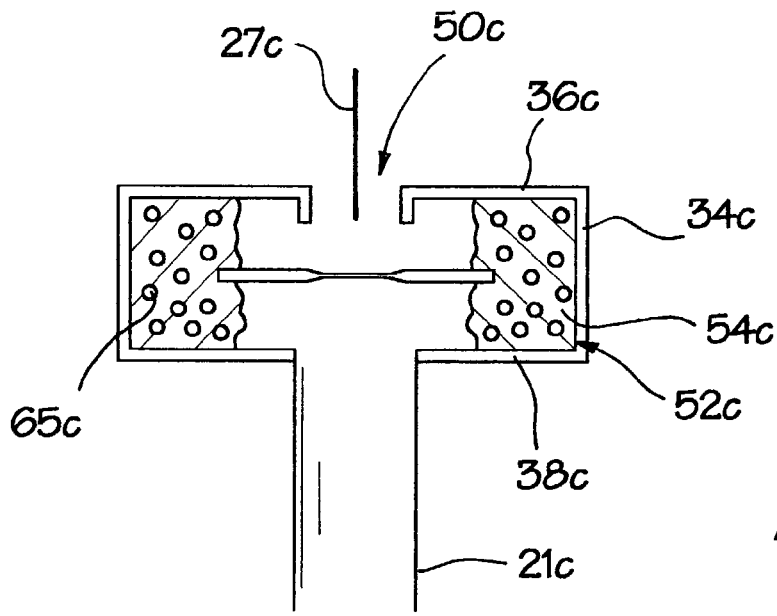
FIG. 6 is an axial cross section view of a valve apparatus with gel material including air pockets.

Another embodiment of the invention is illustrated in FIG. 6, wherein elements of structure similar to those previously disclosed are designated with the same reference numeral followed by the lower case letter "c." In this embodiment, which may include the septum 70c, the block 52c of gel material 54c forms the housing seal 55c around the axis 27c with each of the housing walls 34c, 36c, and 38c. The expansion voids 65c can be formed as air pockets within the gel material 54c of the block 52c. In such an embodiment, the block 52c is generally compressible, like a sponge, as the gel material 54c can expand into the voids 56c to reduce the volume of the block 52c. With this compressibility, flotation of the valve assembly 50c, can be greatly increased with respect to the axis 27c.

Figure 7:
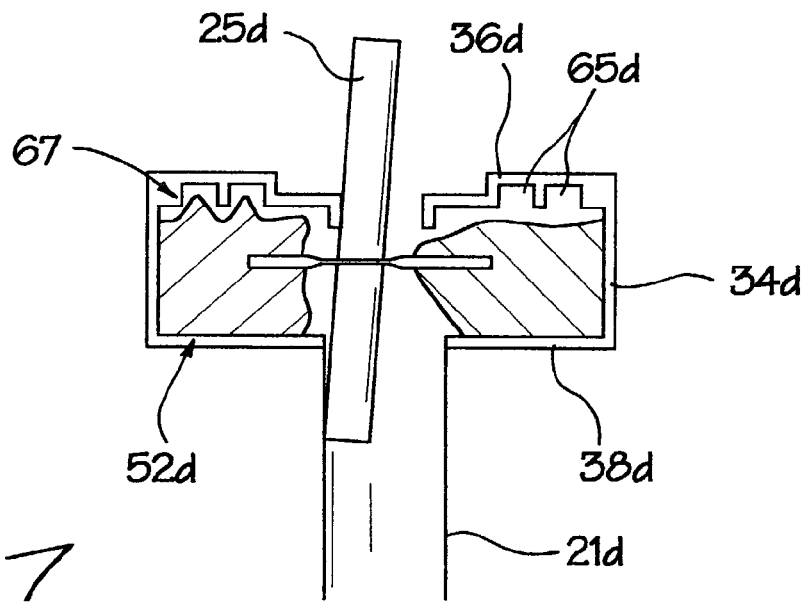
FIG. 7 is an axial cross section view of a further embodiment illustrating air pockets formed in the seal housing.

In the embodiment of FIG. 7, elements of structure similar to those previously disclosed are designated with a the same reference numeral followed by the lower case letter "d." This embodiment differs from those previously disclosed in that the voids 65d are formed permanently within the walls of the housing 23d. For example, the voids 65d can be formed in the horizontal wall 36d to accommodate upward expansion of the gel block 52d, as illustrated by an arrow 67. In this embodiment, the elastomeric septum 70 is insert molded with the gel block 52d, and the housing seal 55 is formed between the gel block 52d and the walls 34d and 38d.

Having disclosed these particular embodiments, it will be understood that many modifications can be made without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims

The invention claimed is:

1. A trocar having an axis and being adapted to provide access for a surgical instrument across a body wall and into a body cavity, comprising:
   a cannula disposed along the axis and having a proximal end and a distal end, the cannula being adapted for disposition across the body wall;
   a housing disposed along the axis at the proximal end of the cannula, the housing having a housing wall adapted to receive the surgical instrument generally along the axis and to introduce the surgical instrument into the cannula;
   a valve disposed in the housing and having properties for forming a first seal with the housing wall and a second seal with the surgical instrument when the surgical instrument is present in the trocar and a third seal when the surgical instrument is absent from the trocar; and
   a gel material inserted in the valve and having floating or off-axis movement properties relative to the axis and to maintain the second seal even when the surgical instrument is inserted or moved laterally from the axis, the first seal being formed by direct contact between the gel material and the housing wall, and the second seal being formed by direct contact between the gel material and the surgical instrument when the surgical instrument is present.

2. The trocar recited in claim 1, wherein the gel material of the valve has a maximum outer dimension measured laterally from the axis and a thickness measured along the axis, the ratio of the maximum outer dimensions to the thickness being in a range between one and five.

3. The trocar recited in claim 2, wherein the thickness is in a range between about five to ten millimeters.

4. The trocar recited in claim 1, further comprising:
   means defining at least one cavity adjacent the gel material, the cavity providing a void into which the gel material can move.

5. The trocar recited in claim 4, wherein the cavity defining means includes a portion of the housing wall.

6. The trocar recited in claim 4, wherein the cavity defining means includes a portion of the gel material.

7. A trocar having an axis and being adapted to provide access for a surgical instrument across a body wall and into a body cavity, comprising:
   a cannula disposed along the axis and having a proximal end and a distal end, the cannula being adapted for disposition across the body wall;
   a housing disposed along the axis at the proximal end of the cannula, the housing having a housing wall adapted to receive the surgical instrument generally along the axis and to introduce the surgical instrument into the cannula;
   a septum valve disposed in the valve housing and adapted to form a first seal with the instrument when the instrument is received into the trocar; and
   a valve support disposed between the septum valve and the housing to float the septum valve laterally from the axis of the trocar, the valve support including a gel material having properties for moving relative to the axis and having elongation greater than 1000 percent to facilitate maintenance of the first seal during off-axis insertion or movement of the instrument relative to the housing.

8. The trocar recited in claim 7, wherein the septum valve is insert molded to the valve support.

9. The trocar recited in claim 7, wherein the valve support forms a second seal with the housing wall.

10. The trocar recited in claim 9, wherein the housing includes:
    a first wall disposed generally parallel to the axis of the trocar; and
    a second wall disposed generally perpendicular to the axis of the trocar.

11. The trocar recited in claim 10, wherein the valve support forms the second seal with the first walls of the housing.

12. The trocar recited in claim 10, wherein the valve support forms the second seal with the second walls of the housing.

13. A trocar having an axis and being adapted to provide access for a surgical instrument across a body wall and into a body cavity, comprising:
    a cannula having a tubular configuration and extending between a proximal end and a distal end;
    a valve housing disposed at the proximal end of the cannula;
    a valve disposed in the valve housing along the axis, the valve being adapted to form a seal with the instrument when the instrument is inserted through the valve housing and into the cannula; and portions of the valve including a gel material having properties for floating or moving off-axis relative to the axis of the trocar to maintain the seal with the instrument when the instrument is inserted or moved laterally from the axis of the trocar, the seal with the instrument being formed by direct contact between the gel material and the surgical instrument when the surgical instrument is present.

14. The trocar recited in claim 13, wherein the properties of the gel material include an elongation of greater than 1000 percent.

15. The trocar recited in claim 13, further comprising:
means defining a void in proximity to the gel material to facilitate movement of the gel material relative to the axis.

16. The trocar recited in claim 15, wherein the void defining means includes portions of the seal housing.

17. The trocar recited in claim 15, wherein the void defining means includes portions of the gel material in the form of air pockets within the gel material.

* * * * *